United States Patent [19]
Brufani et al.

[11] Patent Number: 5,306,825
[45] Date of Patent: Apr. 26, 1994

[54] PHYSOSTIGMINE DERIVATIVES WITH ACETYLCHOLINESTERASE INHIBITION PROPERTIES, AND THE RELATIVE PRODUCTION PROCESS

[75] Inventors: Mario Brufani, Castel Gandolfo; Claudio Castelland, Rome; Maurizio Marta, Rome; Alberto Oliverio, Rome; Flaminia Pavone, Rome; Massimo Pomponi, Rome, all of Italy

[73] Assignee: Consiglio Nazionale Delle Ricerche, Rome, Italy

[21] Appl. No.: 343,282

[22] Filed: Apr. 26, 1989

Related U.S. Application Data

[60] Division of Ser. No. 929,516, Nov. 12, 1986, Pat. No. 4,831,115, which is a continuation-in-part of Ser. No. 705,009, Feb. 25, 1985, abandoned, and a continuation-in-part of Ser. No. 909,025, Sep. 17, 1986, abandoned.

[30] Foreign Application Priority Data

Mar. 1, 1984 [IT] Italy ................... 47780 A/84

[51] Int. Cl.⁵ ............................................. C07D 487/04
[52] U.S. Cl. ............................................. 548/429
[58] Field of Search ...................................... 548/429

[56] References Cited

U.S. PATENT DOCUMENTS

| | | | |
|---|---|---|---|
| 2,860,166 | 11/1958 | Newcomer | 560/24 |
| 2,908,530 | 10/1959 | Rudner | 548/429 |
| 3,972,934 | 8/1976 | Marshall | 560/55 |
| 4,120,691 | 10/1978 | Levitt | 71/93 |
| 4,127,405 | 11/1978 | Levitt | 71/93 |
| 4,163,112 | 7/1979 | Stach | 560/31 |
| 4,169,719 | 10/1979 | Levitt | 71/92 |
| 4,190,432 | 2/1980 | Levitt | 71/93 |
| 4,214,890 | 7/1980 | Levitt | 71/90 |
| 4,231,784 | 11/1980 | Levitt | 71/92 |
| 4,257,802 | 3/1981 | Levitt | 71/93 |
| 4,278,679 | 7/1981 | Madison et al. | 514/411 |
| 4,500,342 | 2/1985 | Aya et al. | 71/93 |
| 4,586,951 | 5/1986 | Aya et al. | 71/92 |
| 4,602,941 | 7/1986 | Aya et al. | 71/92 |
| 4,765,985 | 8/1988 | Leeson | 548/429 |
| 4,791,107 | 12/1988 | Hamer | 548/429 |

FOREIGN PATENT DOCUMENTS

| | | | |
|---|---|---|---|
| 154864 | 9/1985 | European Pat. Off. | 548/429 |
| 825042 | 7/1982 | South Africa . | |

OTHER PUBLICATIONS

Barton "Comprehensive Organic Chemistry", vol. 2 p. 1086 (1982).
Yang, Chem. Abs 107, 242543z (1987).
First, Euro. J. Pharm. 83, (1982) 233–241.
Mar., Advanced Organic Chem., 2nd Edition, pp. 349–352 (1988).
The Merck Index, 9th Edition, p. 961 (1976).

Primary Examiner—Mark L. Berch
Attorney, Agent, or Firm—Stevens, Davis, Miller & Mosher

[57] ABSTRACT

Physostigmine derivatives with acetylcholinesterase inhibition properties, of general formula:

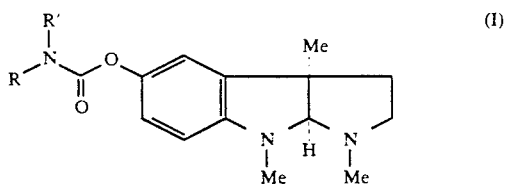

in which R is a linear alkyl of from 2 to 20 C. atoms, a branched alkyl, a cycloalkyl or an aryl, when R' is H, or R and R' are linear alkyl of from 2 to 20 C. atoms.

3 Claims, No Drawings

PHYSOSTIGMINE DERIVATIVES WITH ACETYLCHOLINESTERASE INHIBITION PROPERTIES, AND THE RELATIVE PRODUCTION PROCESS

This is a division of application Ser. No. 06/929,516, filed Nov. 12, 1986 U.S. Pat. No. 4,831,115, which in turn is a continuation-in-part of Ser. No. 06/705,009 filed Feb. 25, 1985 abandoned and a continuation-in-part of Ser. No. 06/909,025, filed Sep. 17, 1986 abandoned.

The present invention relates to physostigmine derivatives with acetylcholinesterase inhibition properties, and the relative production process.

More particularly, the invention relates to a class of physostigmine derivatives of the aforesaid type which is more lipophil than physostigmine and specifically useful in the treatment of Alzheimer's diseases.

Alzheimer's disease is known to be a senile degenerative form of the brain leading to total or partial memory loss, in which there is a significant fall in the cerebral acetylcholine concentration. Drugs able to raise the central level of this latter are therefore used in its treatment. For this purpose, physostigmine or eserine is inter alia used, this being an inhibitor of acetylcholinesterase, the enzyme which hydrolyses acetylcholine in the body. The administration of physostigmine has the drawback of being considerably limited by its high toxicity and its damaging side-effects, particularly towards the digestive system.

There is therefore an obvious requirement for pharmacological products able to provide the therapeutic action of physostigmine, but which are free from the said drawbacks.

To this end, the invention proposes a class of physostigmine derivatives which have a greater lipophil effect and are therefore less active towards the nervous system, and certainly less toxic.

The physostigmine derivatives proposed by the invention are of general formula:

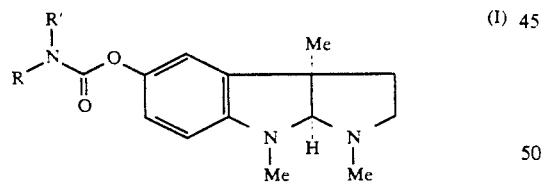

(I)

in which R is a linear alkyl of from 2 to 20 C atoms, a branched alkyl, a cycloalkyl or an aryl, when R' is H, or R and R' are linear alkyl of from 2 to 20 C atoms.

These derivatives are synthesised, according to the invention, starting from physostigmine in accordance with the following schemes:

Scheme I (when R' = H)

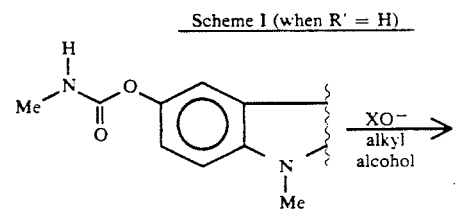

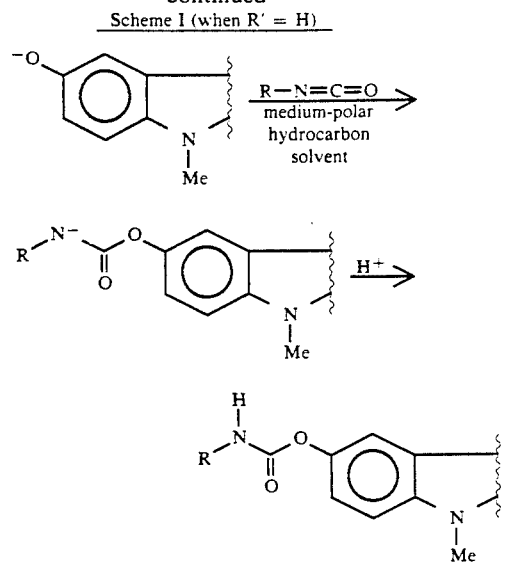

in which X is an alkyl, in particular methyl, the alkyl alcohol is an alcohol with a low number of carbon atoms, in particular ethanol, and the medium-polar hydrocarbon solvent is preferably benzene.

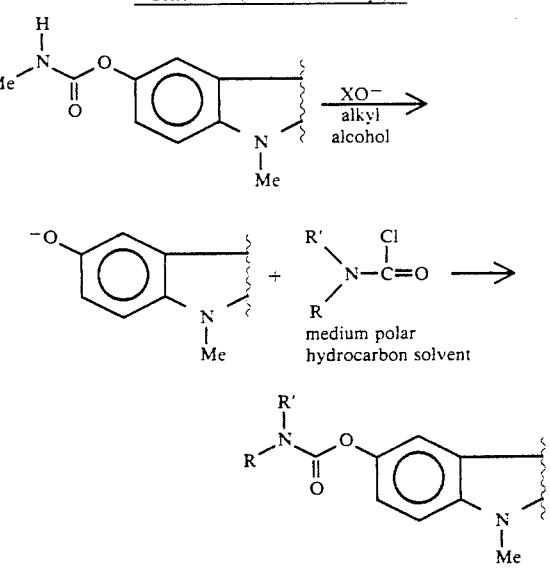

Both the reactions of scheme I and II are conducted under vacuum to prevent eseroline oxidation. The yield is influenced by the choice of solvent.

The best yield is obtained with benzene. The reaction is generally completed in a time of 5 hours and the overall yield varies from 40% to 70%. In some examples, the final yield of the analytically pure product is lower because of the volatility of the isocyanates used when under vacuum.

The crude reaction products can be purified by extraction with solvents such as petroleum ether or n-heptane. The organic solution is washed with aqueous alkaline solutions rapidly under cold conditions, using small solution quantities to prevent carbamate hydrolysis.

Further purification can be carried out by chromatography in a silica gel column, but this also leads to a yield reduction.

The synthetised derivatives were tested "in vitro" on human pseudo-cholinesterase and on acetylcholinesterase originatin from "Electrophorus electricus". Those derivatives in which R is an alkyl chain of small or medium size (up to C=8-10 are as active as physostigmine when under non-stationary "in vitro" conditions f state. Alkyl derivatives with C≧11 and derivatives containing aromatic radicals are less active under the same conditions.

In the following Table the $I_{50}$ values are reported based on the constant of the involved reactions.

The $I_{50}$ values were calculated after 3 minutes using 30 microliters of enzyme at concentrations of 4.6 units/ml. The method is referred in Biochem. Pharm. 7 page 88 (1961). See also Brufani et al. in Italian Journal of Biochemistry n. 5 page 321-34 (1985).

is 35 mg/kg, and the lethal dose 100 (LD100) is 45 mg/kg. Compared with physostigmine, the lethal dose 50 of the heptyl derivative is about 60 times greater, the LD50 for physostigmine being 0.6 mg/mg. The LD50 values were determined within two hours from the injection. Beyond this time, no obvious effects were observable.

The LD50 values of other derivatives according to the present invention, evaluated with the same method resulted as follows:
n.butyl derivative (R'=H, R=n.butyl)=6 mg/kg
n.nonyl derivative (R'=H, R=n.nonyl)=50 mg/kg
dimethyl derivative (R'=R=methyl)=9 mg/kg
diethyl derivative (R'=R=ethyl)=38 mg/kg

SPONTANEOUS LOCOMOTOR ACTIVITY

The test used for measuring the spontaneous locomotor activity was that employing a cage divided into two parts. This test has proved particularly useful in demon-

| Inibitor | $K_a \times 10^6$ ($\pm$S.E.) | $k_2$ ($\pm$S.E.) | $k_i \times 10^{-5}$ ($\pm$S.E.) | $k_3 \times 10^2$ ($\pm$S.E.) | $K_i \times 10^8$ | $I_{50} \times 10^6$ |
|---|---|---|---|---|---|---|
| Eserine | 3.5 ± 0.9 | 8.8 ± 1.0 | 26.6 ± 0.8 | 5.4 ± 0.2 | 2.0 | 0.2 |
| Ethyl- | 15.0 ± 5.8 | 3.5 ± 1.1 | 2.3 ± 0.1 | 2.5 ± 0.3 | 13.0 | 1.0 |
| n.Propyl- | | | 0.9 ± 0.1 | | | 2.5 |
| n.Butyl- | 34.0 ± 20.0 | 6.7 ± 3.5 | 2.0 ± 0.1 | 0.45 ± 0.14 | 2.6 | 3.5 |
| Heptyl- | 2.4 ± 1.3 | 7.2 ± 3.6 | 2.8 ± 0.1 | 0.71 ± 0.08 | 5.3 | 1.0 |
| Nonyl- | | | 1.5 ± 0.1 | | | 1.5 |
| Undecyl- | | | 0.8 ± 0.1 | | | 2.9 |
| Dimethyl- | 54.9 ± 33.8 | 8.8 ± 3.3 | 0.2 ± 0.05 | 8.5 ± 1.2 | 34.8 | 3.1 |
| Diethyl- | | | 0.004 | | | 680.0 |

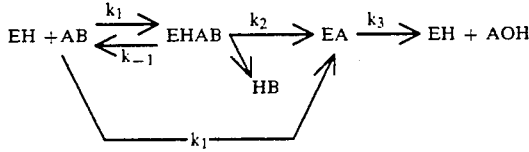

EH is the enzyme; AB is the inhibitor; EHAB is an enzyme-inhibitor binding complex of Michaelis type governed by the constant $K_i$; EA is the irreversibly inhibited enzyme; $k_2$ is the firt order carbamylation rate constant; $k_3$ is the firt order reactivation rate constant; $k_i$ is the bimolecular rate constant; $I_{50}$ is the molar concentration of inhibitor giving 50% inhibition.

The derivative with an alkyl chain in which R=heptyl and R'=H, indicated herein after as "heptyl derivative" was subjected to a pharmacological trial on mice.

The activity of the this product was evaluated in terms of its toxicity (lethal dose: LD) and its behavioural effects.

In particular, with regard to this latter aspect, an evaluation was made of the effects of the substance on spontaneous locomotor activity, and of the antagonisms of the heptyl derivative towards the central stimulating effects of anticholinergic drugs (scopolamine).

An evaluation was also made of the effects of the substance on the electrocorticographic activity and on the inhibition of cerebral acetylcholinesterase (AchE) "in vivo".

The experiments were conducted using male Swiss mice with a weight of about 30 g.

TOXICITY

The acute toxic effects of the heptyl derivative were also evaluated as a comparison with the effects of physostigmine. On the basis of the range of doses administered (minimum doese 5 mg/kg, maximum dose 50 mg/kg) it was established that the lethal dose 50 (LD50)

strating the behavioural effects of substances which act on the central nervous system.

The heptyl derivative does not influence spontaneous activity between a dose of 0.1 mg/kg and a dose of 3 mg/kg. At higher doses, a depressing effect is observed, which at a dose of 5 mg/kg leads to a 25% reduction in locomotor activity compared with the controls. An analogous effect is produced by physostigmine at doses of between 0.1 and 0.3 mg/kg.

ANTAGONISM TOWARDS THE CENTRAL STIMULATING EFFECTS OF ANTICHOLINERGIC DRUGS

At the central cholinergic antagonists exert a stimulating action on spontaneous activity, a study was carried out of the antagonism towards the stimulating effects of scopolamine (a typical anticholinergic drug which acts at the central level) by the heptyl derivative. At a dose of 1 mg/kg, scopolamine induced an evident stimulating effect (100% increase in basic locomotor activity), and this was antagonised by administering 3 mg/kg of heptyl derivative (a dose per se ineffective), which restored the activity to the control values.

These activities show the existence of antagonism towards the central effects of scopolamine, indicative of a central effect of the heptyl derivative.

ELECTROCORTICOGRAPHIC ACTIVITY

In order to further demonstrate the central effects of the heptyl derivative, the modifications induced by it on the cortical electrical activity of mice implanted with parietal electrodes was studies.

The electrocardiogram was recorded by a Beckmann polygraph. 15 minutes after administering 10 mg/kg of the heptyl derivative, a slowing down of the electrocorticographic rate was noted, together with an increase in its amplitude.

These results are further proof of a central effect of the substance. The aforesaid results indicate that the heptyl derivative exert a clear effect on various behavioural parameters and on the electrocorticogram of the animals tested. Further direct and evident proof of its central effects related to the inhibition of cerebral AchE was provided by further experiments, in which the inhibition of AchE by this compound was evaluated using colorimetric histological techniques (Lynch).

Cerebral AchE is normally inhibited by organo-phosphoric esters, which determine an irreversible inhibition, and they are therefore more powerful than eserine, the action of which is reversible.

In the experiment, the effects of diisopropylfluorophosphate, eserine and the heptyl derivative were correlated with respect to control preparations. Whereas eserine had no evident effect at doses of 0.4 and 0.5 mg/kg (doses close to the LD50), AchE inhibition by diisopropylfluorophosphate resulted in the lack of coloration of the cerebral tissues. At a dose of 20 mg/kg, the heptyl derivative produced an evident diminution in the coloration of the cerebral tissues of mice injected with a solution of the substance 15 minutes before being sacrificed. At a dose of 30 mg/kg, this effect was even more marked, and remained for more than one hour after injecting the heptyl derivative.

This latter result indicated in an evident manner that the heptyl derivative provides AchE inhibition at the cerebral level, showing that the effects of the substance on behaviour are not related only to possible peripheral effects.

The acetylcholinesterase (AchE) inhibition in the brain and serum was tested for the heptyl derivative in comparison with physostigmine. Both physostigaine and heptyl derivative were used in form of salycilate and dissolved in distilled water with carbossimethyl cellulose sodium salt at 2%. From the results reported in Table I and II it is possible to notice that the activity of physostigmine measured after 10 minutes is higher than that of heptyl derivative but the duration of the activity is much lower and after 120 minutes becomes insignificant.

TABLE I

Acetylcholinesterase (AChE) inhibition in the brain and serum 10 min. after i.p. administration of different doses of physostigmine and heptyl to rats

| | Dose mg/kg i.p. | No. | AChE inhibition (%) M ± SE | | $ID_{50}$ (mg/Kg) i.p. | |
|---|---|---|---|---|---|---|
| | | | Brain | Serum | Brain | Serum |
| Phys. | 0.10 | 4 | 19.58 ± 11.43 | 19.55 ± 8.29 | 0.19 | 0.20 |
| | 0.15 | 4 | 39.18 ± 4.32 | 32.93 ± 11.34 | | |
| | 0.20 | 4 | 53.70 ± 8.30 | 53.68 ± 2.41 | | |
| Hept. | 0.50 | 4 | 25.55 ± 11.64 | 20.85 ± 5.64 | 1.39 | 1.10 |
| | 1.00 | 4 | 50.00 ± 1.32 | 59.40 ± 1.99 | | |
| | 2.00 | 4 | 53.62 ± 10.51 | 67.42 ± 4.29 | | |
| | 4.00 | 4 | 72.35 ± 5.92 | 79.42 ± 2.89 | | |

Control enzyme activity is 8.38 ± 0.76 moles acetylcholine hydrolyzed/min/g. brain and 0.37 ± 0.03 moles acetylcholine hydrolized/min/ml/serum (N = 10).
Phys.: physostigmine;
Hept.: heptyl derivative.

TABLE II

Acetylcholinesterase (AChE) inhibition in the brain and in serum after i.p. administration of equiactive doses of physostigmine and heptyl, at various time intervals (10–60–120 min.) after dosing.

| | Dose mg/Kg i.p. | % AChE Inhibition at minutes M ± SE (n = 4) | | | | | |
|---|---|---|---|---|---|---|---|
| | | 10 | | 60 | | 120 | |
| | | brain | serum | brain | serum | brain | serum |
| Phys. | 0.2 | 53.70 ± 8.30 | 53.68 ± 2.41 | 12.47 ± 2.83 | 9.82 ± 6.83 | 3.28 ± 1.99 | 2.58 ± 1.49 |
| Hept. | 1.0 | 50.00 ± 1.32 | 59.40 ± 1.99 | 28.46 ± 9.56 | 41.15 ± 4.29 | 22.45 ± 2.54 | 21.53 ± 2.31 |
| Statistical | t | 0.3744 | 1.7323 | 1.6038 | 3.8844 | 5.9430 | 6.8938 |
| comparison | p | NS | NS | NS | <0.02 | <0.005 | <0.001 |

The physostigmine derivatives of the invention characterized by a less polar property owing to the presence of alkyl or cycloalkyl or aryl groups instead of methyl group, although their inhibitory activity is lower, show a duration of the inhibitory activity much longer than that of physostigaine as ti results from Table II.

The physostigmine derivatives according to the invention can be properly converted into the corresponding salts of pharmacologically acceptable acids, useful for preparing therapeutic compositions.

The salts are obtained combining in stoichiometric ratio the physostigmine derivative with the acid.

The present invention is described hereinafter for non-limiting illustrative purposes, with particular reference to the following examples.

The described thin chromatography (TLC) was carried out on $F_{254}$ type 60 aluminum plates of 0.2 mm thickness (Merck).

The UV spectra wavelength is expressed in nanometers, the absorption, in parentheses, being expressed as ε.

The IR spectra values are expressed in $cm^{-1}$. The NMR spectra were determined with a spectrometer at 60 MHz, using TMS as internal reference. The δ values are in parts per million (p.p.m.).

The mass spectra were determined with an AEI 12 spectrometer. The melting points were determined with a mnual Kofler apparatus, and the $[\alpha]_D^{25}$ rotatory powers were determined with a Perkin Elmer 253 polarimeter.

EXAMPLE 1

Preparation of trimethyl-1,3a,8-hexahydro-1,2,3a,8-,8a-pyrrol[2,3-b] indole-5(3aS, 8aR) propylcarbamate: $C_3E$ 550 mg (2 mmoles) of eserine and 108 mg (2 mmoles) of sodium methoxide are placed in a flask (50 ml) to which a vacuum of between 5 and 10 mmHg is applied.

70 ml of absolute ethanol are then added over 2 hours in small volumes, under agitation at ambient temperature. When the ethanol has been removed, 50 ml of benzene are added operating under the same conditions, and the solvent is removed by operating in a temperature range of between 25° and 35° C. To this residue are then slowly added 50 ml of a benzene solution containing 4 mmoles of propyl isocyanate, and the reaction mixture is left to stand for 3 hours, adding benzene when necessary. During this time, the eseroline is converted to carbamate. The benzene is evaporated, and 20 ml of petroleum ether are added to the reaction residue, followed by 10 ml of $10^{-3}M$ HCl. The vacuum is removed at this point, and the crude reaction product extracted with diethyl ether after previous saturation with sodium bicarbonate. The combined ether solutions are rapidly extracted with 50 ml of HCl 0.05N. The aqueous acid solution, saturated with sodium bicarbonate, is again extracted but with petroleum ether, and the organic layer is repeatedly washed with water before being dried over sodium sulphate. The solvent is finally removed under vacuum. If necessary, the extract is chromatographed over a silica gel column, using chloroform/methanol (98/2) as eluent, to give the pure carbamate which on subjection to TLC (chloroform/methanol=9/1), and using iodine detection, gives a brown stain having an $R_F$ practically equal to that of eserine.

The product is finally dissolved in benzene, heptane is added, and the solution cooled. A residue slowly crystallises having an M.P. of 83°–86° C.

UV spectrum is methanol: $C_3E$: 311 (3350), 253 (14200).

IR spectrum in chloroform: $C_3E$: 3450 (m), 3200 (m), 2950 (m), 1720 (s), 1480 (s), 1330 (m), 1250 (s), 1200 (s), 1170 (m), 1120 (m), 1110 (m), 950 (m).

NMR spectrum in deuterated chloroform: $C_3E$: 1.00 (t), 1.20–1.80 (m), 1.50 (s), 2.00 (t), 2.60 (s), 2.90 (s), 2.90–3.50 (m), 4.15 (s), 4.80–5.20 (m), 6.30 (dd), 6.70 (d), 6.75 (dd).

Mass spectrum: $C_3E$: 303 (20), 218 (100), 174 (45), 161 (43), 160 (42). $[\alpha]_D^{25}$ −81° (c=1.7 in methanol).

EXAMPLE 2

Preparation of trimethyl-1,3a,8-hexahydro-1,2,3,3a,8-,8a-pyrrol[2,3-b]indole-5(3aS, 8aR) isopropylcarbamate: $iC_3E$; the procedure of Example 1 is followed.

UV spectrum in methanol: $iC_3E$: 309 (3300), 251 (14100).

IR spectrum in potassium bromide: $iC_3E$: 3200 (m), 2900 (m), 1720 (m), 1600 (m), 1550 (m), 1480 (s), 1430 (m), 1330 (m), 1250 (s), 1200 (s), 1160 (s), 1110 (m), 1030 (m), 930 (s), 870 (m).

NMR spectrum in deuterated benzene: $iC_3E$: 0.90 (d), 1.30 (s), 1.80 (t), 2.30 (s), 2.50 (t), 2.55 (s), 3.90 (ept), 4.05 (s), 4.40–4.70 (m), 6.25 (d), 7.00 (d), 7.05 (dd).

Mass spectrum: $iC_3E$: 303 (10), 218 (100), 174 (40), 161 (31), 160 (33).

EXAMPLE 3

Preparation of trimethyl-1,3a,8-hexahydro-1,2,3,3a,8-,8a-pyrrol[2,3-b]indole-5(3aS, 8aR) tert-butylcarbamate: the procedure of Example 1 is followed: the residue is crystallised from heptane; M.P. 69°–73° C.

UV spectrum is methanol: $tC_4E$: 310 (3300), 253 (14000).

IR spectrum in chloroform: $tC_4E$: 3440 (m), 2920 (m), 2860 (m), 1720 (s), 1550 (m), 1480 (s), 1420 (m), 1330 (m), 1250 (m), 1180 (m), 1100 (s), 950 (m), 900 (s).

NMR spectrum in deuterated benzene: $tC_4E$: 1.25 (s), 1.35 (s), 1.80 (t), 1.30 (s), 2.45 (t), 2.60 (s), 3.30 (s), 3.95 (s), 6.15 (d), 6.65 (d), 6.77 (dd), 8.75–9.10 (m).

Mass spectrum: $tC_4E$: 317 (15), 218 (100), 174 (43), 161 (30), 160 (36). $[\alpha]_D^{25}$ −71° (c=1.5 in methanol).

EXAMPLE 4

Preparation of trimethyl-1,3a,8-hexahydro-1,2,3,3a,8-,8a-pyrrol[2,3-b] indole-5(3aS, 8aR) phenylcarbamate: PhE; the precedure of Example 1 is followed; the residue is crystallised from heptane; M.P. 92°–96° C.

UV spectrum in methanol: PhE: 284 (13000).

IR spectrum in chloroform: PhE: 3430 (m), 2920 (m), 1740 (s), 1600 (m), 1520 (m), 1330 (m), 1180 (s), 1110 (m), 900 (s).

NMR spectrum in deuterated chloroform: PhE: 1.40 (s), 1.95 (t), 2.55 (s), 2.70 (t), 2.90 (s), 3.40–3.70 (m), 4.10 (s), 6.30 (d), 6.75 (d), 6.90 (d), 7.00–7.40 (m).

Mass spectrum: PhE: 337 (10), 218 (100), 174 (46), 162 (10), 161 (31), 160 (38).

EXAMPLE 5

Preparation of trimethyl-1,3a,8-hexahydro-1,2,3,3a,8-,8a-pyrrol[2,3-b] indole-5(3aS, 8aR) cyclohexylcarbamate: $cC_6E$; the procedure of Example 1 is followed.

UV spectrum in methanol: $cC_6E$; 308 (2300), 251 (11500).

IR spectrum in chloroform: $cC_6E$: 3450 (m), 3200 (s), 2930 (s), 2850 (m), 1730 (s), 1660 (m), 1480 (s), 1250 (s), 1200 (s), 1100 (m).

NMR spectrum in deuterated chloroform: $cC_6E$: 1.15–1.85 (m), 1.45 (s), 2.00 (t), 2.60 (s), 2.80 (t), 2.90 (s), 3.30–3.70 (m), 4.15 (s), 4.50–5.00 (m), 6.35 (d), 6.75 (s), 6.85 (dd).

Mass spectrum: $cC_6E$: 343 (23), 218 (100), 188 (10), 175 (20), 173 (64), 162 (17), 161 (58), 160 (56).

EXAMPLE 6

Preparation of trimethyl-1,3a,8-hexahydro-1,2,3,3a,8-,8a-pyrrol[2,3-b] indole-5(3aS, 8aR) heptylcarbamate: $C_7E$; the procedure of Example 1 is followed. When all the solvent has been removed by distillation under vacuum, the oily residue is slowly crystallised under cold conditions from heptane; M.P. 60°–64° C.

UV spectrum in methanol: $C_7E$: 303 (3300), 253 (14200).

IR spectrum in chloroform: $C_7E$: 3460 (m), 2920 (s), 2860 (s), 1720 (s), 1670 (s), 1600 (s), 1490 (s), 1240 (s), 1200 (s), 1120 (m).

NMR spectrum in deuterated benzene: $C_7E$: 0.90 (t), 1.25 (s), 1.35 (s), 1.80 (t), 2.40 (t), 2.50 (t), 2.60 (s), 3.35 (q), 4.00 (s), 5.30–5.70 (m), 6.20 (d), 7.00 (s), 7.05 (dd).

Mass spectrum: C$_7$E: 359 (15), 218 (100), 174 (30), 161 (28), 160 (29).

EXAMPLE 7

Preparation of trimethyl-1,3a,8-hexahydro-1,2,3,3a,8-,8a-pyrrol[2,3-b] indole-5(3aS, 8aR) undecylcarbamate: C$_{11}$E; the procedure of Example 1 is followed. On evaporating the solvent, an oily residue remained but was not crystallised.

UV spectrum in methanol: C$_{11}$E: 305 (330), 251 (14150).

IR spectrum in chloroform: C$_{11}$E: 3450 (m), 2920 (s), 2850 (m), 1725 (s), 1435 (s), 1200 (m), 1100 (m).

NMR spectrum in deuterated benzene: C$_{11}$E: 0.90 (t), 1.25 (s), 1.40 (s), 2.00 (t), 2.50 (s), 2.80 (t), 2.90 (s), 2.95–3.30 (m), 4.30 (s), 5.00–5.30 (m), 6.25 (dd), 6.65 (d), 6.75 (dd).

Mass spectrum: C$_{11}$E: 41 (13), 219 (25), 218 (100), 174 (28), 161 (24), 160 (30).

EXAMPLE 8

Preparation of trimethyl-1,3a,8-hexahydro-1,2,3,3a,8-,8a-pyrrol[2,3-b]indole-5(3aS, 8aR) pentadecylcarbamate: C$_{15}$E; the procedure of Example 1 is followed, but with the difference that sulphuric acid is used instead of hydrochloric acid. An oily residue is obtained.

UV spectrum in methanol: C$_{15}$E: 303 (2760), 253 (11550).

IR spectrum in chloroform: C$_{15}$E: 3450 (w), 2920 (s), 2840 (m), 1720 (s), 1480 (m), 1400 (s), 1200 (m), 1100 (m).

NMR spectrum in carbon tetrachloride: C$_{15}$E: 0.90 (t), 1.25 (s), 1.40 (s), 1.90 (t), 2.40 (s), 2.35–2.80 (m), 2.85 (s), 2.85–3.30 (m), 4.05 (s), 5.50–5.70 (m), 6.15 (s), 6.60 (s), 6.50–6.75 (m).

Mass spectrum: C$_{15}$E: 471 (3), 218 (100), 174 (26), 161 (22), 160 (23).

The present invention has been described with particular reference to some specific embodiments, but modifications can be made thereto by experts of the art without leaving the relative scope of protection.

EXAMPLE 9

Pyrrolo [2,3-b]indol-5-ol,3,3a,8,8a-hexahydro-1,3a,8-trimethyl-dimethylcarbamate (ester),(3aS-cis). Working as in Example 1 except that the isocyanate was substituted with the dimethyl carbamyl chloride.

M.p. 81°–83° C.; IR (CHCl$_3$) 1705, 1610, 1485, 1390, 1270, 1180 cm$^{-1}$; UV (CH$_3$OH), $\lambda_{max}$312 (lg$\epsilon$=4.56) and 255 (lg$\epsilon$=2.56) nm; $^1$H NMR (deuterobenzene) $\delta$ 1.40 (s, 3H,), 1.90 (m, 2H), 2.35 (s, 3H) 2.55 (m, 2H) 2.85 (s, 3H)) 3.00 (s, 6H, N(CH$_3$)$_2$), 4.10 (s, 1H), 6.20 (dd, 1H, J$_{para}$=1.5 Hz, J$_{ortho}$=8.0 Hz), 6.60 (d, 1H, J=1.5 Hz), 6.70 (dd, 1H, J$_{para}$=1.5 Hz, J$_{ortho}$=8.0 Hz); MS, m/e 289 (M$^+$, 100).

EXAMPLE 10

Pyrrolo [2,3-b]indol-5-ol,3,3a,8,8a-hexahydrol,3a,8-trimethyl-diethylcarbamate (ester), (3aS-cis). Working as for dimethyl-, derivative of Example 9 but with diethyl carbamyl chloride. M.p. 79° C.; IR (CHCl$_3$) 1710, 1615, 1490, 1400, 1290 cm$^{-1}$; UV (CH$_3$OH) $\lambda_{max}$311 (lg$\Gamma$=4.40) and 254 (lg$\epsilon$=2.50) nm; $^1$H NMR (deuterobenzene) $\delta$ 1.05 (d, 3H, J=7 Hz), 1.15 (d, 3H, J=7 Hz), 1.35 (s, 3H), 1.80 (m, 2H), 2.40 (s, 3H), 2.55 (m, 2H), 2.65 (s, 3H), 3.20 (q, 4H, J=7 Hz), 4.00 (s, 1H), 6.25 (d, 1H, J$_{para}$=1.5 Hz, J$_{ortho}$=8.0 Hz), 6.95 (d, 1H, J=1.5 Hz), 7.05 (q, 1H, J$_{para}$=1.5 Hz, J$_{ortho}$=8.0 Hz); MS m/e 317 (M$^+$, 100).

We claim:

1. A process for preparing physostigmine derivatives with acetylcholinesterase inhibition properties, of the following formula:

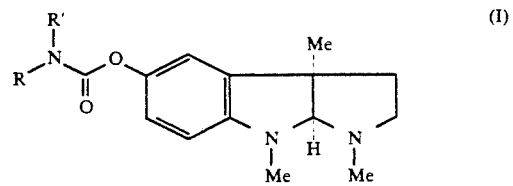

in which R is selected from the group consisting of propyl, isopropyl, tert-butyl, phenyl, cyclohexyl, heptyl, undecyl and pentadecyl when R' is H or R and R' are both ethyl or methyl, in accordance with the following schemes:

Scheme I (when R' = H)

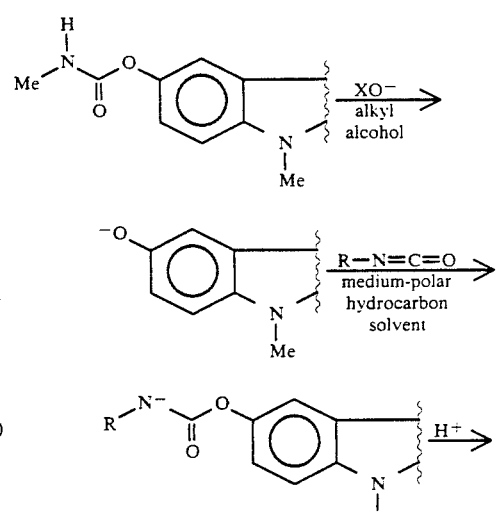

Scheme II (when R' = alkyl)

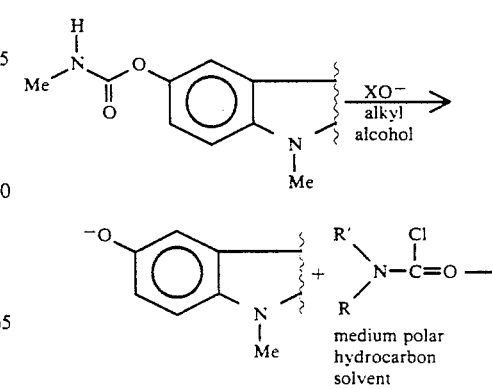

-continued
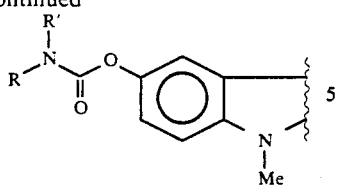
wherein X is methyl.
2. A process for preparing physostigmine derivatives as claimed in claim 1, in which the alkyl alcohol is ethanol and the medium-polar hydrocarbon solvent is benzene.
3. A process for preparing physostigmine derivatives as claimed in claim 1, characterised in that the reaction is carried out under vacuum.